(12) United States Patent
Yoshikawa et al.

(10) Patent No.: US 8,764,955 B2
(45) Date of Patent: Jul. 1, 2014

(54) GAS SENSOR

(75) Inventors: Takaya Yoshikawa, Kasugai (JP);
Tomohiro Tajima, Kasugai (JP);
Hisaharu Nishio, Tokai (JP); Masao Tsuzuki, Kakamigahara (JP); Kunihiko Yonezu, Mie (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 13/187,945

(22) Filed: Jul. 21, 2011

(65) Prior Publication Data
US 2012/0018305 A1    Jan. 26, 2012

(30) Foreign Application Priority Data

Jul. 22, 2010  (JP) ................................ 2010-164477

(51) Int. Cl.
*G01N 27/406* (2006.01)
*G01N 27/407* (2006.01)
*G01N 27/409* (2006.01)

(52) U.S. Cl.
CPC ............ *G01N 27/406* (2013.01); *G01N 27/407* (2013.01); *G01N 27/4078* (2013.01); *G01N 27/409* (2013.01)
USPC ........... 204/424; 204/425; 204/426; 204/427; 73/23.31; 73/23.32

(58) Field of Classification Search
USPC .................. 204/424–429; 73/23.31–23.32
See application file for complete search history.

(56) References Cited

U.S. PATENT DOCUMENTS

| | | | | | |
|---|---|---|---|---|---|
| 4,383,907 | A | * | 5/1983 | Legrand et al. | 204/426 |
| 4,399,017 | A | * | 8/1983 | Inoue et al. | 204/425 |
| 5,711,863 | A | * | 1/1998 | Henkelmann et al. | 204/428 |
| 5,817,920 | A | * | 10/1998 | Kuisell et al. | 73/23.31 |
| 6,068,746 | A | * | 5/2000 | Kojima et al. | 204/421 |
| 2001/0047938 | A1 | * | 12/2001 | Nelson et al. | 204/426 |
| 2002/0043548 | A1 | * | 4/2002 | Evers et al. | 228/44.7 |
| 2003/0226412 | A1 | * | 12/2003 | Rumminger et al. | 73/866.5 |
| 2009/0126456 | A1 | | 5/2009 | Matsuo et al. | |
| 2012/0055234 | A1 | | 3/2012 | Yonezu et al. | |

FOREIGN PATENT DOCUMENTS

| | | |
|---|---|---|
| DE | 102008055129 A1 | 7/2010 |
| DE | 112004000050 B4 | 6/2011 |
| EP | 0828156 A2 | 3/1998 |
| JP | 10-132779 A | 5/1998 |
| JP | 3873390 B2 | 1/2007 |
| JP | 2011-131090 | 6/2011 |

* cited by examiner

*Primary Examiner* — Bach Dinh
(74) *Attorney, Agent, or Firm* — Sughrue Mion, PLLC

(57) ABSTRACT

A gas sensor (200) includes a gas sensor element (10) extending in the direction of an axis O, and a housing (50) made of metal, radially surrounding the gas sensor element, and adapted for inserting at least partially into a sensor-mounting hole (350) of a mounting body (300). The gas sensor (200) further includes a resin member (60, 61) which radially surrounds the housing at least partially and having a contact portion (C) in contact with the housing that is at least partially disposed axially frontward with respect to the outer surface of the mounting body (300) around the sensor-mounting hole, and a heat sink member (80) that is in contact with the housing at an axial position the same as or located frontward of the axial position of the front end of the contact portion.

8 Claims, 13 Drawing Sheets

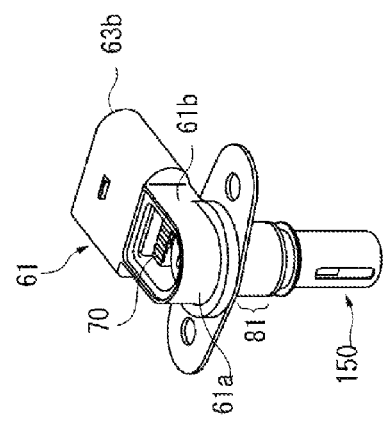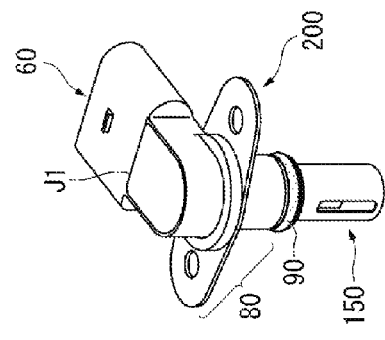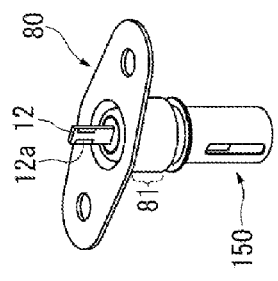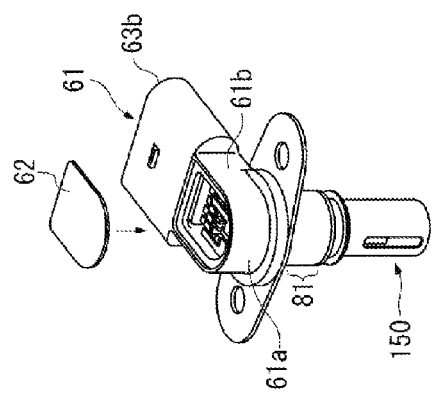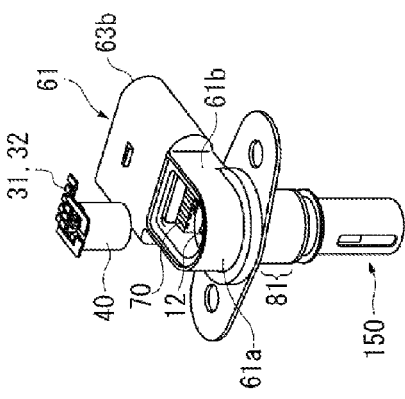

GAS SENSOR

BACKGROUND OF THE INVENTION

1. Field of the Invention

The present invention relates to a gas sensor having a gas sensor element for detecting the concentration of a particular gas.

2. Description of the Related Art

A gas sensor is mounted to an intake system (e.g., an intake pipe or an intake manifold) of an internal combustion engine, such as a diesel engine or a gasoline engine, in order to control, for example, the condition of combustion by monitoring the concentration of a particular gas. Conventionally, such a gas sensor has the following structure: a gas detection element is held in a housing made of metal, and various terminals, a separator, etc., provided at a proximal side (rear side) of the housing are protected with a tubular cover made of metal.

However, the cover made of metal is problematic in that, since the structure is intricate, manufacture or assembly consumes time and labor. In order to cope with this problem, a structure has been developed as described in Patent Document 1 in which a base member made of resin is connected to a proximal end portion of the housing.

Meanwhile, in order to mitigate the impact imposed on a colliding object with which a vehicle having an internal combustion engine collides, a clearance must be provided between the hood and engine parts. In this connection, the length of outward projection of the gas sensor from the intake pipe must be shortened.

[Patent Document 1] Japanese Patent Application Laid-Open (kokai) No. H10-132779

3. Problems to be Solved by the Invention

However, in the gas sensor having a base member made of resin, in order to shorten the length of outward projection of the gas sensor from the intake pipe with the length (size) of the gas detection element being held unchanged, the gas sensor must be inserted deeper into the intake pipe. As a result, the connection between the base member and the housing is positioned within a sensor mounting hole of the intake pipe.

Meanwhile, according to the gas sensor of Patent Document 1, the heat of a heater for heating the gas detection element, the heat of intake gas, etc., are transmitted directly to the intake pipe from the housing, thereby reducing thermal influence on the base member. However, a problem arises with the above-mentioned configuration: since the heat is partially transmitted to the intake pipe from the housing via the above-mentioned connection, a large thermal load (e.g., 200° C. or higher) is imposed on a front end portion of the base member made of resin.

SUMMARY OF THE INVENTION

It is therefore an object of the present invention to provide a gas sensor having a structure in which a resin member radially covers a housing at least partially, wherein the length of outward projection of the gas sensor from a body to which the gas sensor is to be mounted (hereinafter, referred to as a mounting body) is shortened and thermal influence of the housing on the resin member is reduced, thereby improving durability.

The above object has been achieved by providing a gas sensor which comprises a gas sensor element extending in the direction of an axis O and having a detection portion provided at the front end thereof for detecting a particular gas component in a gas to be measured, and a housing made of metal, the housing radially surrounding the gas sensor element, and adapted for inserting at least partially into a sensor-mounting hole of a mounting body. The gas sensor further comprises a resin member which radially surrounds the housing at least partially and having a contact portion in contact with the housing that is at least partially disposed axially frontward with respect to an outer surface of the mounting body around the sensor-mounting hole, and a heat sink member that is in contact with the housing at an axial position that is the same as or located frontward of an axial position of the front end of the contact portion, and adapted to radiate heat of the housing to the outside of the gas sensor.

According to the thus-configured gas sensor, since at least a portion of the contact portion is disposed axially frontward (inward) with respect to the outer surface of the mounting body around the sensor-mounting hole, the length of outward projection of the gas sensor from the mounting body can be shortened.

Heat of the heater for heating the gas sensor element, heat of intake gas, and like heat are radiated from the housing to the outside of the gas sensor by means of the heat sink member, which is in contact with the housing at an axial position the same as or located frontward of an axial position of the front end of the contact portion. Thus, heat of the housing is hardly transmitted to a front end portion, which serves as a connection portion, of the resin member, whereby thermal influence on the resin member can be reduced.

Regarding a configurational feature for radiating heat of the housing to the outside of the gas sensor by means of the heat sink member, preferably, a rear end portion of the heat sink member is exposed outward of the outer surface of the mounting body around the sensor-mounting hole.

According to the thus-configured gas sensor, heat transmitted to the housing from the heater for heating the gas sensor element, an intake gas, etc., passes through the heat sink member and is then radiated to the outside of an mounting body (to the atmosphere), from the rear end portion of the heat sink member, the rear end portion being exposed axially outward of the outer surface of the mounting body around the sensor-mounting hole. Thus, thermal influence on the resin member is reduced. As a result, durability of the gas sensor is further improved.

Regarding a further configurational feature for radiating heat of the housing to the outside of the gas sensor by means of the heat sink member, preferably, a portion of the heat sink member is in contact with the inner wall of the sensor-mounting hole.

According to the thus-configured gas sensor, heat transmitted to the housing from the heater for heating the gas sensor element, an intake gas, etc., passes through the heat sink member and is then radiated from the inner wall of the sensor-mounting hole to the mounting body. Thus, thermal influence on the resin member is reduced. As a result, durability of the gas sensor is further improved.

Preferably, a rear end portion of the heat sink member assumes the form of a flange for mounting to the mounting body.

According to the thus-configured gas sensor, the gas sensor can be reliably secured to the mounting body, and the area of contact between the heat sink member and the mounting body can be increased. Thus, heat of the housing is more effectively radiated to the mounting body, through the flange, which is a rear end portion of the heat sink member. Also, since the flange is exposed axially outward of the outer surface of the mounting body around the sensor-mounting hole, heat of the housing is effectively radiated to the outside of the mounting body. Therefore, durability of the gas sensor is further improved.

Preferably, the resin member has a connector portion.

According to the thus-configured gas sensor, there is no need to provide, separately from the resin member, a connector for electrically connecting the gas sensor and an external apparatus, and the length of outward projection of the resin member including the connector from the mounting body can be further shortened.

Preferably, the front end of the contact portion is located between the inner and outer surfaces of the mounting body.

If the gas sensor is inserted excessively deep into the sensor-mounting hole for shortening the length of outward projection of the gas sensor from the mounting body, the front end of the contact portion may be located axially frontward with respect to the axially inner surface of the mounting body and may thus be exposed to a high-temperature gas. Thus, by locating the front end of the contact portion being located axially outward of the axially inner surface of the mounting body, the contact portion is restrained from assuming an excessively high temperature. Accordingly, durability of the gas sensor is further improved.

Preferably, the heat sink member is made of a material having a thermal conductivity higher than that of the resin member.

According to the thus-configured gas sensor, even when the axial position of contact between the heat sink member and the housing coincides with the axial position of the front end of the contact portion, heat of the housing is transmitted to the heat sink member rather than to the resin member. Thus, the contact portion of the resin member is restrained from assuming an excessively high temperature. Accordingly, durability of the gas sensor is further improved.

Thus, the present invention provides a gas sensor in which the length of outward projection of the gas sensor from a mounting body is shortened and in which the thermal influence of the housing on the resin member is reduced, thereby improving durability.

BRIEF DESCRIPTION OF THE DRAWINGS

FIGS. 5A to 5E are process drawings showing an example method of manufacturing the gas sensor according to the first embodiment.

DESCRIPTION OF REFERENCE NUMERALS

Figure 1:
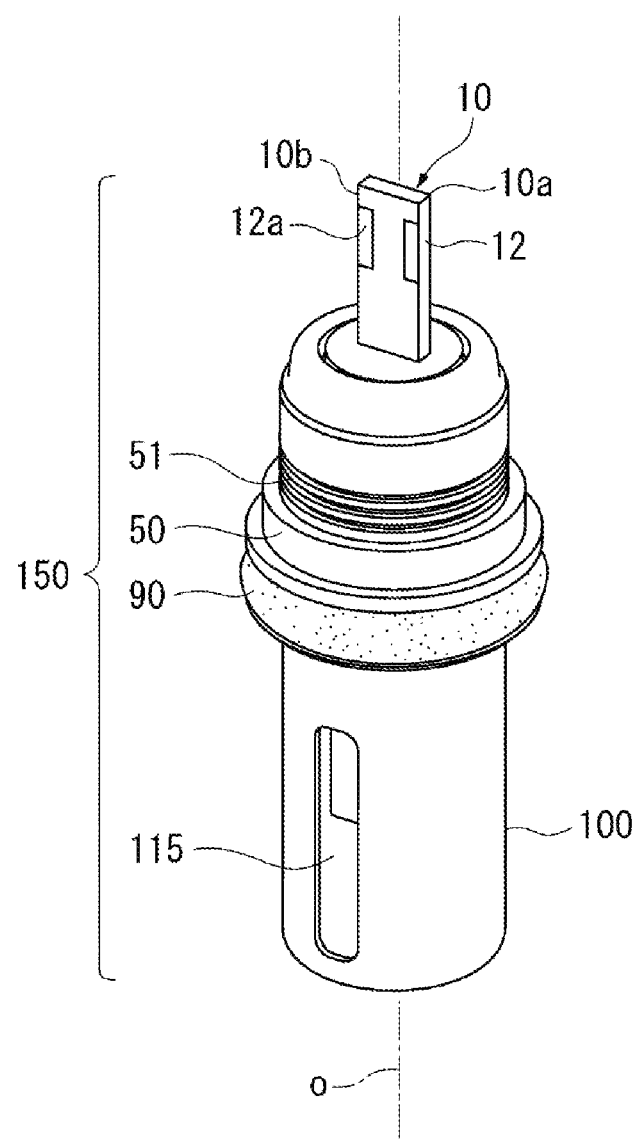
FIG. 1 is a perspective view of an element assembly held within a gas sensor according to a first embodiment of a first aspect of the invention.

Reference numerals used to identify various structural features in the drawings including the following.

200, 210, 220: gas sensor
10: gas sensor element
11: detection portion
50: housing
60: resin member
63: connector portion
80, 180, 180$x$: heat sink member
82: flange portion
300: mounting body
350: sensor-mounting hole
360: inner wall of mounting body
BS2: mating surface
A: outer surface of mounting body
C: joint portion

DETAILED DESCRIPTION OF THE PREFERRED EMBODIMENTS

Preferred embodiments of the present invention will next be described with reference to the drawings. However, the present invention should not be construed as being limited thereto.

Figure 2:
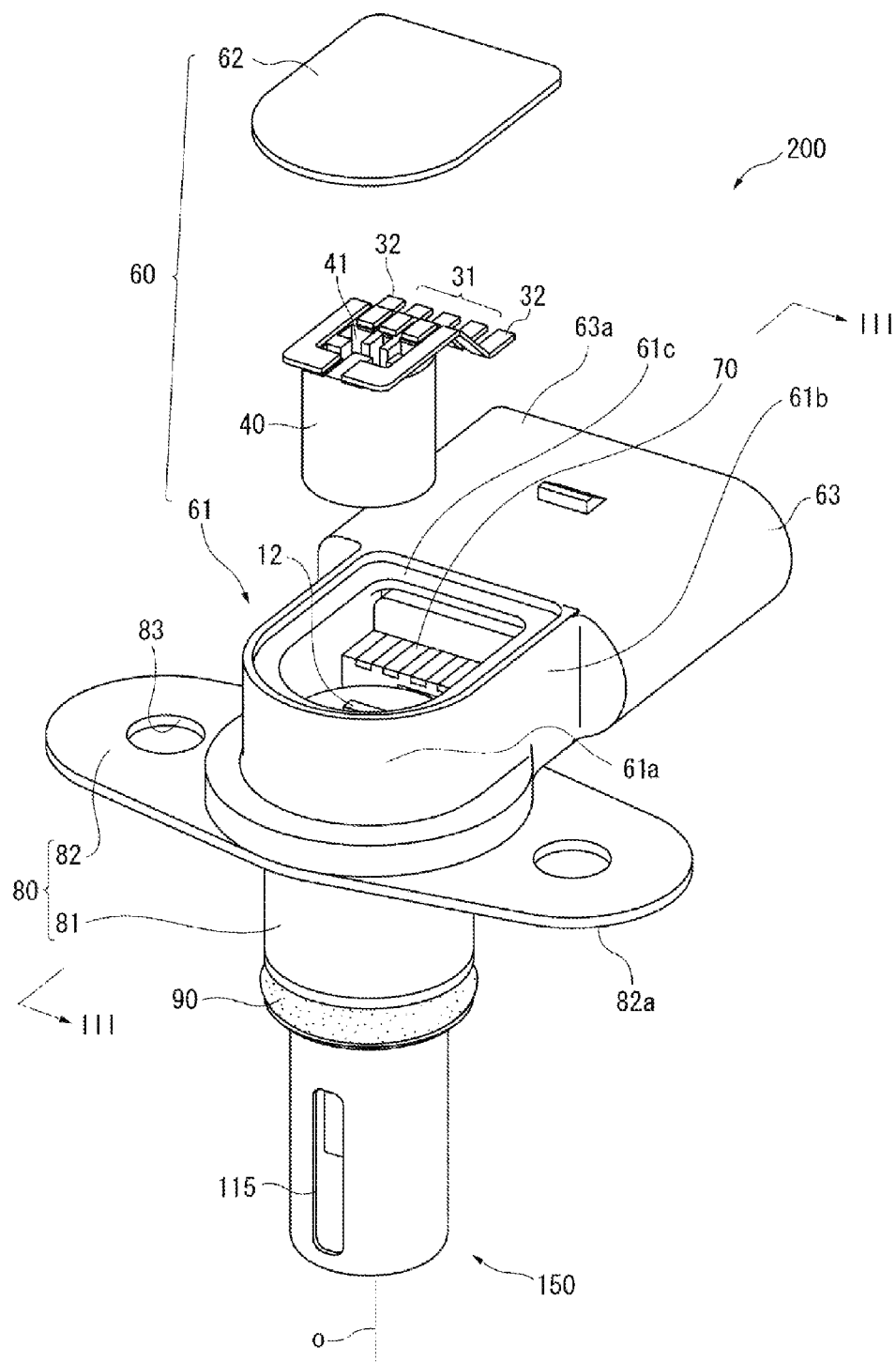
FIG. 2 is a perspective view showing the configuration of the gas sensor according to the first embodiment.
Figure 3:
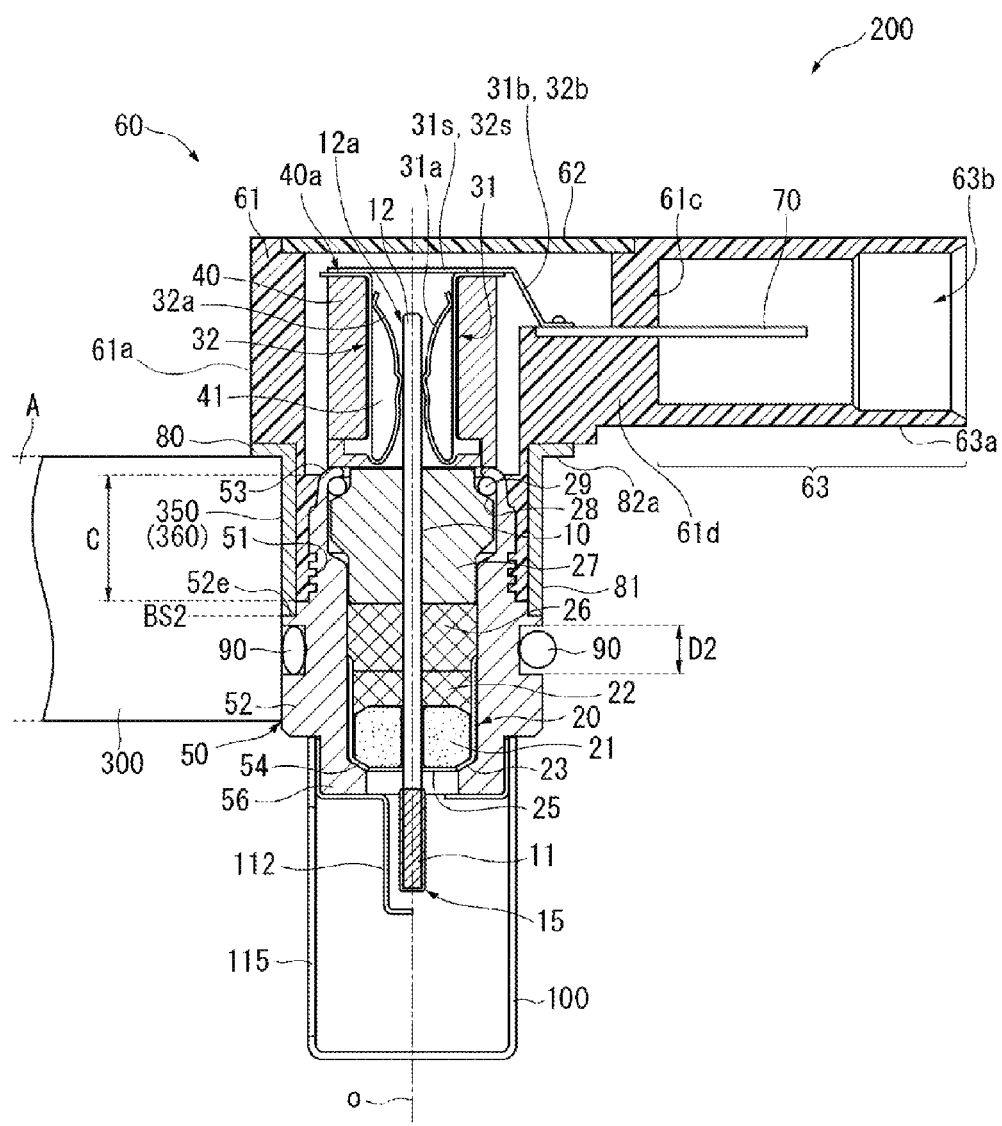
FIG. 3 is a sectional view taken along line III-III of FIG. 2.

FIG. 1 is a perspective view showing an example of the schematic configuration of an element assembly 150 held within a gas sensor 200 according to a first embodiment of a first aspect of the present invention; FIG. 2 is a perspective view of the gas sensor 200 according to the first embodiment; and FIG. 3 is a sectional view taken along line III-III of FIG. 2.

In FIG. 1, the direction of an axis O (represented by the dash-dot line) of a gas sensor element 10 coincides with the vertical direction. In the following description, a side toward a rear end portion 12 is referred to as the rear side of the gas sensor element 10 (and of the gas sensor), and an opposite side toward a detection portion of the gas sensor element 10 is referred to as the front side of the gas sensor element 10 (and of the gas sensor). A direction perpendicular to the direction of the axis O is referred to as a "radial direction."

As shown in FIG. 2, the gas sensor 200 includes the element assembly 150 (including the gas sensor element 10); a resin member 60 joined to a housing 50 (see FIG. 1) of the element assembly 150; a heat sink member 80 made of metal and radially surrounding a front end portion of the resin member 60; a separator 40 made of ceramic and accommodated within the resin member 60; and connection terminals 31 and 32 attached to the separator 40. In the present first embodiment, the resin member 60 is composed of a resin member body 61 fixed to the housing 50 through insert molding, and a cover 62 fitted to the resin member body 61 from the rear side for closing the internal space of the resin member body 61. A seal member (O ring) 90 is externally fitted into a groove circumferentially formed in a front end portion of the housing 50.

As described below, the resin member body 61 of the resin member 60 is joined to the housing 50, and the cover 62 of the resin member 60 is not joined to the housing 50. Thus, accurately, the resin member body 61 corresponds to the "resin member" of the invention. However, in the following description, the resin member 60 including the resin member body 61 corresponds to the "resin member" of the invention.

The gas sensor element 10 is a publicly known substantially rectangular columnar laminate which extends in the direction of the axis O. In the gas sensor element, a detection element for detecting an oxygen concentration and a heater for promptly activating the detection element through application of heat are bonded together. The detection element is configured such that a solid electrolyte member which contains zirconia as a main component, and a pair of electrodes which contain platinum as a main component, are laminated together via an insulation layer having a hollow measuring chamber formed therein. More specifically, the detection element has an oxygen pump cell and an oxygen-concentration-measuring cell. The oxygen pump cell is configured as follows: one of a pair of electrodes formed on the respective opposite sides of a solid electrolyte member is exposed outward, whereas the other electrode is exposed to the measuring chamber. The oxygen-concentration-measuring cell is configured as follows: one of a pair of electrodes formed on the respective opposite sides of a solid electrolyte member is exposed to the measuring chamber, whereas the other electrode is exposed to a reference gas chamber. Current to be applied between the paired electrodes of the oxygen pump cell is controlled in such a manner that an output voltage of the oxygen-concentration-measuring cell assumes a predetermined value, thereby pumping oxygen out from the measuring chamber or pumping oxygen into the measuring chamber from outside.

In the oxygen pump cell, the pair of electrodes and a portion of the solid electrolyte member sandwiched between the electrodes collectively serve as a detection portion 11 in which current flows according to the concentration of oxygen. A rear end portion 12 of the gas sensor element 10 has five electrode pads 12a (FIG. 1 shows two of them formed on a second surface 10b of the gas sensor element 10, and the remaining three are formed on a first surface 10a not shown in FIG. 1) formed thereon for leading out output signals from the detection element and for supplying power to the heater.

As shown in FIG. 3, a closed-bottomed tubular metal cup 20 is disposed slightly frontward of the axial center of the gas sensor element 10 in such a manner that the gas sensor element 10 is inserted through the interior of the metal cup 20 with the detection portion 11 projecting from an opening 25 formed in the bottom of the metal cup 20. The metal cup 20 is a member for holding the gas sensor element 10 in the housing 50. A front-end peripheral portion 23 located at a peripheral portion of the bottom of the metal cup 20 is tapered toward a tubular wall portion of the metal cup 20. The metal cup 20 contains a ceramic ring 21 made of alumina and a talc ring 22 formed by compacting a talc powder, in such a manner that the gas sensor element 10 is inserted through the ceramic ring 21 and through the talc ring 22. The talc ring 22 is compacted within the metal cup 20 so as to tightly fill an associated space, thereby holding the gas sensor element 10 in position in the metal cup 20.

An assembly of the metal cup 20 and the gas sensor element 10 is radially surrounded by and held by the housing 50 made of metal, the housing 50 being inserted into a sensor-mounting hole 350 of a mounting body 300. The housing 50 is formed from stainless steel such as SUS430. The housing 50 has a large-diameter portion 52 having the largest outside diameter and located substantially at the central position with respect to the direction of the axis O of the housing 50. The housing 50 also has a stepped portion 52e formed rearward of the rear end of the large-diameter portion 52 so as to be reduced in diameter in two steps. Furthermore, the housing 50 has an array of grooves 51 located rearward of the stepped portion 52e, formed on the outer circumferential surface thereof, and arranged in the direction of the axis O. The array of grooves 51 enhances attachment of the housing 50 to the resin member 60 by a wedge effect. The housing 50 further has a crimp portion 53 located rearward of the array of grooves 51. The crimp portion 53 is adapted to hold the gas sensor element 10 in the housing 50 by means of crimping.

The housing 50 has a groove D2 formed in a circumferentially continuous manner on the outer surface of the large-diameter portion 52. A seal member (O ring) 90 is externally fitted into the groove D2.

The housing 50 further has a front-end engagement portion 56 located frontward of the large-diameter portion 52. An outer protector 100, described below, engages the front-end engagement portion 56. The housing 50 has an inner stepped portion 54 on its inner circumferential surface at a position substantially corresponding to the front-end engagement portion 56. The front-end peripheral portion 23 of the metal cup 20, which holds the gas sensor element 10, engages the inner stepped portion 54. Furthermore, a talc ring 26 is placed into the housing 50 along the inner circumference of the housing 50 toward the rear end of the metal cup 20 in such a state that the gas sensor element 10 is inserted through the talc ring 26. A tubular sleeve 27 is fitted into the housing 50 in such a manner as to press the talc ring 26 from the rear end of the talc ring 26. The sleeve 27 has a step-like shoulder portion 28 formed on the outer circumferential surface of a rear end portion of the sleeve 27. An annular crimp packing 29 is disposed on the shoulder portion 28.

The crimp portion 53 of the housing 50 is crimped in such a manner as to press the shoulder portion 28 of the sleeve 27 frontward via the crimp packing 29. By forming the crimp portion 53, the talc ring 26 pressed through the sleeve 27 is compacted within the housing 50, thereby tightly filling an associated space. By means of the talc ring 26 and the talc ring 22, which is previously placed in the metal cup 20, the metal cup 20 and the gas sensor element 10 are held in position in the housing 50 in a gastight manner.

Referring back to FIG. 2, the heat sink member 80 integrally has a cylindrical heat sink casing portion 81 and two semicircular flange portions 82 (corresponding to the "rear end portion of the heat sink member" of the invention) extending radially outward from the rear end of the heat sink casing portion 81. Each of the flange portions 82 has a through-hole 83. Screws are inserted through the respective through-holes 83 and screwed into respective threaded holes formed in the mounting body 300 (e.g., an intake system of an internal combustion engine) (see FIG. 3), whereby the gas sensor 200 is mounted to the mounting body 300. Frontward-oriented surfaces (back surfaces) 82a of the flange portions 82 are flush with each other and come into close contact with the outer surface of the mounting body 300 (see FIG. 3).

The outside diameter of the heat sink casing portion 81 is equal to the outside diameter of the large-diameter portion 52 of the housing 50. The inside diameter of the heat sink casing portion 81 is substantially equal to the outside diameter of the wall surface of an outer stepped subportion of the stepped portion 52e. Thus, when a rear portion of the housing 50 is covered with the heat sink casing portion 81, the front end of the heat sink casing portion 81 is closely fitted to the outer stepped subportion of the stepped portion 52e, and the outer surface of the heat sink casing portion 81 and the outer surface of the large-diameter portion 52 are flush with each other. Furthermore, a clearance corresponding to the radial dimension of an inner stepped subportion of the stepped portion 52e is formed between the inner surface of the heat sink member 80 and a portion of the housing 50 extending from the array of grooves 51 to the crimp portion 53. In this condition, a mating surface BS2 between the stepped portion 52e and the front end of the heat sink casing portion 81 is subjected to full-circle laser welding or the like, whereby the heat sink member 80 radially surrounds a rear portion of the housing 50.

The heat sink member 80 can be formed from, for example, aluminum, an aluminum alloy, or stainless steel. The heat sink member 80 may be higher or lower in thermal conductivity than the housing 50. However, preferably, the heat sink member 80 is higher in thermal conductivity than the resin member 60, described below.

Next, the resin member 60 will be described with reference to FIGS. 2 and 3. In the present embodiment, the resin member body 61 is formed from a nylon resin, which is a resin of good moldability, through insert molding into the above-mentioned clearance between the housing 50 and the heat sink member 80. Particularly, by means of the resin member body 61 and the housing 50 being joined together via the array of grooves 51, which collectively have a large surface area, by virtue of the wedge effect, attachment and sealing performance between the resin member body 61 and the housing 50 are improved.

The front end of the resin member body 61 is in contact with the inner stepped subportion of the stepped portion 52e of the housing 50. A region extending from the inner stepped subportion of the stepped portion 52e to the vicinity of the crimp portion 53 serves as a joint portion C between the resin member body 61 and the housing 50. In the example of FIG. 3, the entire joint portion C is disposed axially frontward (inward) with respect to the outer surface of the mounting body 300 around the sensor-mounting hole 350 (i.e., a mounting surface A) and corresponds to the "contact portion" of the invention. The heat sink member 80 (the heat sink casing portion 81 thereof) radially surrounds the contact portion (the joint portion C) fully. The mating surface BS2 is located frontward of the front end of the joint portion C with respect to the direction of the axis O.

On the rear side of the crimp portion 53, the resin member body 61 has a semicylindrical portion 61a having a diameter greater than that of the large-diameter portion 52 of the housing 50 and oriented toward the same side as that toward which a gas introduction hole 115 is formed in the outer protector 100. Also, two wall portions 61b extend in parallel from the respective ends of the semicylindrical portion 61a toward a side opposite the gas introduction hole 115. A partition wall 61c extends between and perpendicularly to the wall portions 61b at the ends of the wall portions 61b. Thus, the semicylindrical portion 61a, the two wall portions 61b, and the partition wall 61c radially surround the rear end portion 12 of the gas sensor element 10. The semicylindrical portion 61a, the two wall portions 61b, and the partition wall 61c are slightly higher in axial height than the rear end portion 12 of the gas sensor element 10. Accordingly, the rear end portion 12 (also, the separator 40 and connector terminals 70) is accommodated within an internal space of the resin member body 61.

Furthermore, the resin member body 61 integrally has a rectangular male connector portion 63 extending outward in a radial direction of the gas sensor 200 and having an opening 63b on a side opposite the gas introduction hole 115, which will be described later. The connector portion 63 is configured such that a connector wall 63a which defines the opening 63b surrounds the connector terminals 70 extending in the connector portion 63 and is integrally connected to the partition wall 61c. Furthermore, the ends of the connector terminals 70 of the connector portion 63 are exposed from the partition wall 61c to the internal space of the resin member 60.

Meanwhile, the gas sensor element 10 is disposed as follows: the rear end portion 12 projects rearward of the rear end (the crimp portion 53) of the housing 50 and is covered with a tubular separator 40 made of an insulating ceramic. A reception hole 41 of the separator 40 accommodates the electrode pads 12a provided on the rear end portion 12 of the gas sensor element 10. The connection terminals 31 and 32 disposed within the reception hole 41 are electrically connected to the corresponding electrode pads 12a. Ends of the connection terminals 31 and 32 (external-circuit connection terminal ends, described below) disposed externally of the separator 40 extend in a radial direction and are electrically connected to the corresponding connector terminals 70.

As mentioned above, the electrode pads 12a of the gas sensor element 10 and the connector terminals 70 are electrically connected via the connection terminals 31 and 32. In this condition, the cover 62 is fitted to the resin member body 61, and then the two members are joined together (through, for example, fusion). By this procedure, the separator 40 is covered with the resin member 60, thereby yielding the gas sensor 200.

Meanwhile, the detection portion 11 of the gas sensor element 10 is coated with a porous protection layer 15 so as to protect externally exposed electrodes of the detection portion 11 from poisoning and water adhesion caused by intake gas or the like. The outer protector 100 is fitted to and laser-welded to the front-end engagement portion 56 of the housing 50, thereby being fixed in position. The outer protector 100 protects the detection portion 11 accommodated therein.

Meanwhile, the outer protector 100 has the gas introduction hole 115 formed therein and adapted to expose the detection portion 11 of the gas sensor element 10 to gas. The gas introduction hole 115 assumes the form of a slit extending in the axial direction. By employing the gas introduction hole 115 in the form of a slit, gas contained in the outer protector 100 is promptly renewed, thereby restraining deterioration in the detection accuracy of the gas sensor element 10. In the first embodiment, the gas introduction hole 115 has a width of 1.0 mm. In this manner, when the gas introduction hole 115 has a width of 0.5 mm or greater, gas contained in the outer protector 100 is promptly renewed, whereby deterioration in gas detection accuracy can be prevented.

When the gas sensor 200 is mounted to an intake system of an internal combustion engine, orienting the gas introduction hole 115 toward the downstream direction of the intake system can restrain the generation of cracking in the gas sensor element 10 and can restrain deterioration in the detection accuracy of the gas sensor 200.

Thus, it is good practice to fix the heat sink member 80 to a rear portion of the housing 50 while the extending direction of the flange portions 82 and the orientation of the gas introduction hole 115 are adjusted in such a manner that, when the gas sensor 200 is mounted, the gas introduction hole 115 is oriented toward the downstream direction of the intake system.

Furthermore, an inner protector 112 is disposed within the outer protector 100 between the detection portion 11 and the gas introduction hole 115 so as to restrain direct exposure of the detection portion 11 to gas which is introduced into the outer protector 100 through the gas introduction hole 115. Thus, adhesion of water and oil contained in gas to the gas sensor element 10 and the generation of cracking in the gas sensor element 10 can be restrained. Also, the adhesion of soot contained in gas to the gas sensor element 10 can be restrained. Therefore, deterioration in the detection accuracy of the gas sensor 200 can be restrained.

Next, the configuration of the electrically conductive members 31, 32, and 70 will be described with reference to FIGS. 3 and 4.

The connection terminals 31 and 32 are formed as follows: strip-like electrically conductive members (metal pieces) are stamped out by use of a press or the like, and the conductive members thus obtained are bent into a predetermined shape. The connection terminals 31 and 32 integrally have element connection-terminal portions 31*a* and 32*a* disposed within the reception hole 41 of the separator 40 and connected to the corresponding electrode pads 12*a*, and external-circuit connection-terminal portions 31*b* and 32*b* for connecting the element connection-terminal portions 31*a* and 32*a* to the connector terminals 70.

The element connection-terminal portions 31*a* and 32*a* have lead subportions 31*t* and 32*t* extending along the wall surface of the reception hole 41, and contact subportions 31*r* and 32*r* bent at the front ends of the lead subportions 31*t* and 32*t* and bulging, for providing elastic force, toward a center plane which contains the axis of the separator 40. When the rear end portion 12 of the gas sensor element 10 is inserted into the reception hole 41 of the separator 40, the element connection-terminal portions 31*a* and 32*a* (the contact subportions 31*r* and 32*r*) come into sliding contact with the corresponding electrode pads 12*a*, and the elastic force of the element connection-terminal portions 31*a* and 32*a* increases the pressure of contact with the electrode pads 12*a*, thereby ensuring reliable electrical connection.

The external-circuit connection-terminal portions 31*b* and 32*b* will next be described in detail.

Each of the external-circuit connection-terminal portions 31*b* integrally has a horizontal subportion 31*s* extending from the lead subportion 31*t* via a first bent subportion 31*e* and extending in a radial direction along an upper surface 40*a* of the separator 40; a first terminal subportion 31*b*1 extending from the horizontal subportion 31*s* via a second bent subportion 31*f* in such an obliquely extending manner as to extend toward the axial center of the separator 40 and radially outward; and a second terminal subportion 31*b*2 extending from the first terminal subportion 31*b*1 horizontally and radially outward via a third bent subportion 31*g*.

Each of the external-circuit connection-terminal portions 32*b* integrally has a horizontal subportion 32*s* extending from the lead subportion 32*t* via a first bent subportion 32*e* and extending in a radial direction along the upper surface 40*a* of the separator 40; a first terminal subportion 32*b*1 extending from the horizontal subportion 32*s* via a second bent subportion 32*f* in such an obliquely extending manner as to extend toward the axial center height of the separator 40 and radially outward; and a second terminal subportion 32*b*2 extending from the first terminal subportion 32*b*1 horizontally and radially outward via a third bent subportion 32*g*.

The first terminal subportions 31*b*1 and the first terminal subportions 32*b*1 have the same angle of inclination. The second terminal subportions 31*b*2 and the second terminal subportions 32*b*2 are arrayed in a row.

Figure 4:
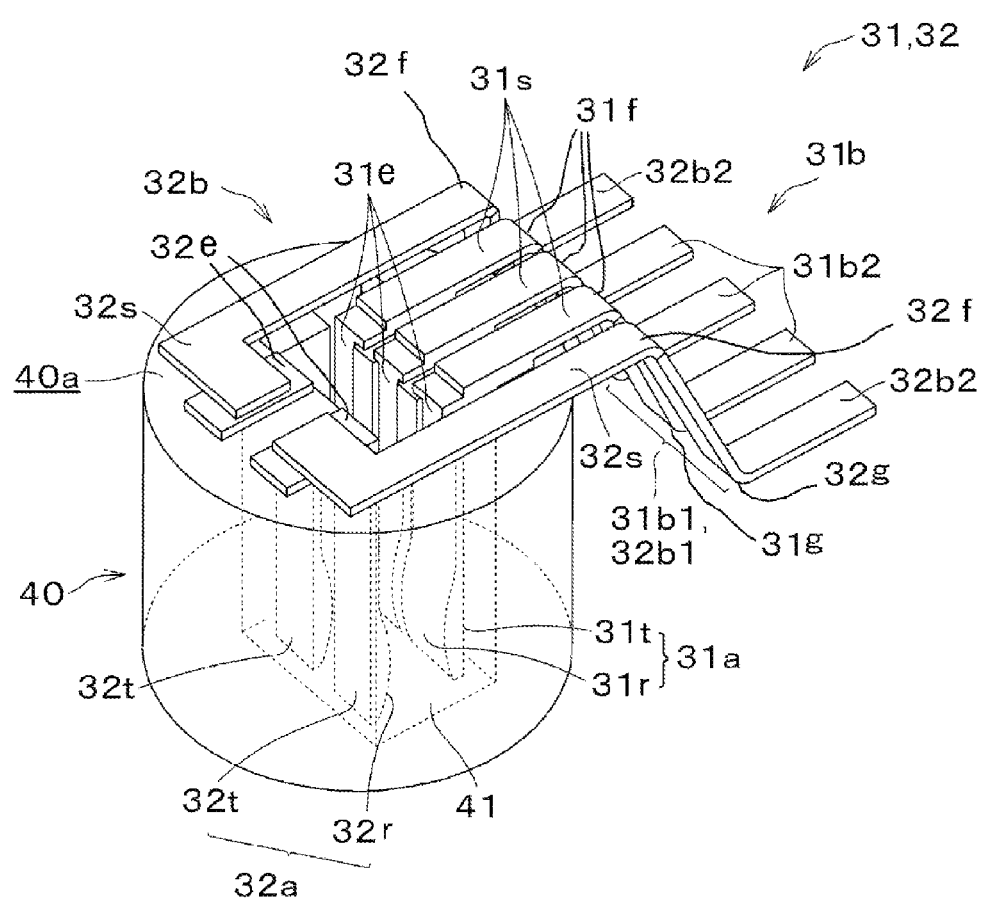
FIG. 4 is a perspective view showing the configuration of connection terminals of the gas sensor according to the first embodiment.

The horizontal subportions 31*s* of the connection terminals 31 extend straight from the reception hole 41 of the separator 40 toward the far side of FIG. 4. By contrast, in order to avoid contact with the horizontal subportions 31*s*, the horizontal subportions 32*s* of the connection terminals 32 extend on a side toward the circumference of the reception hole 41 and extend straight from outside the three horizontal subportions 31*s* toward the far side of FIG. 4.

In this manner, the connection terminals 31 and 32 extend in a radial direction from the rearward-oriented upper surface 40*a* of the separator 40. Namely, the connection terminals 31 and 32 and lead wires, etc., to be connected to the connection terminals 31 and 32 do not project rearward from the rearward-oriented upper surface 40*a* of the separator 40. Thus, the height of the gas sensor 200 along the direction of the axis O is lowered accordingly, whereby the length of projection of the gas sensor 200 from a mounting body as measured when the gas sensor 200 is mounted to the mounting body can be shortened.

Since the external-circuit connection-terminal portions 31*b* and 32*b* are bent toward the axial center of the separator 40, the axial height of the connector terminals 70 connected to the bent ends of the external-circuit connection-terminal portions 31*b* and 32*b* can be lowered frontward. The connector portion 63 has an outline that projects rearward and frontward with respect to the connector terminals 70 for allowing a mating connector to be radially fitted into and removed from the connector portion 63. However, by lowering the positional height of the connector terminals 70, the positional height of the connector portion 63 is lowered accordingly. Thus, the height of the gas sensor 200 as measured along the direction of the axis O is lowered accordingly, the length of projection of the gas sensor 200 from a mounting body as measured when the gas sensor 200 is mounted to the mounting body can be shortened.

Next a mode for mounting the thus-configured gas sensor 200 to the mounting body 300 and the working effects of the gas sensor 200 according to the first embodiment will be described.

First, the seal member 90 attached to the housing 50 is greater in outside diameter than the large-diameter portion 52, and the mounting body 300; i.e., a body to which the gas sensor is to be mounted, has a sensor-mounting hole 350, which is slightly greater in diameter than the large-diameter portion 52. Thus, when the gas sensor 200 is inserted, for mounting, from its front end into the sensor-mounting hole 350, the seal member 90 is squeezed by an inner wall 360 of the sensor-mounting hole 350, thereby providing a seal between the housing 50 and the mounting body 300.

As shown in FIG. 3, the frontward-oriented surfaces (back surfaces) 82*a* of the flange portions 82 are in contact with the outer surface (the mounting surface A) of the mounting body 300. Furthermore, screws are inserted through the respective through-holes 83 of the flange portions 82 and threadingly engage respective threaded holes formed in the mounting body 300, whereby the gas sensor 200 is mounted to the mounting body 300.

In this manner, at least a portion (in this example, the entirety) of the joint portion C (contact portion) between the housing 50 and the resin member 60 (the resin member body 61) is disposed axially frontward (inward) with respect to the outer surface of the mounting body 300 around the sensor-mounting hole 350 (i.e., the mounting surface A). Thus, the length of outward projection, from the mounting body 300, of the gas sensor 200 including the resin member 60 can be shortened. Notably, a portion of the housing 50 may be located axially outward of the outer surface of the mounting body 300 around the sensor-mounting hole 350.

The heat sink member 80 (the heat sink casing portion 81 thereof) radially surrounds the joint portion C. Also, while the front end of the heat sink casing portion 81 is in contact with the housing 50 at a position located frontward of the joint portion C, the flange portions 82 integral with the heat sink casing portion 81 are exposed outward (rearward) of the outer surface of the mounting body 300 around the sensor-mounting hole 350 (i.e., the mounting surface A). Thus, heat of the housing 50, whose temperature becomes high, is radiated to the atmosphere through the heat sink member 80 (particularly through the flange portions 82). By virtue of this heat transfer mechanism, heat does not stagnate in the joint portion C, which is a portion of the resin member 60 subjected to the highest thermal load, thereby reducing thermal influence on the resin member 60 (the resin member body 61).

The position where the heat sink member 80 and the housing 50 are in contact with each other may coincide with the axial position of the front end of the joint portion C or may be located frontward of the front end of the joint portion C. However, in order to reduce thermal influence on the resin member 60, the more frontward the contact position is located as viewed in the axial direction, the better. The heat sink member 80 surrounds (covers) the joint portion C as viewed from radial directions. However, the heat sink member 80 may cover the joint portion C while leaving uncovered portions as viewed along the circumferential direction, instead of covering fully along the circumferential direction.

Particularly, in the case where the mounting body 300 is made of resin, even though the heat sink casing portion 81 is in contact with the inner wall 360 of the sensor-mounting hole 350, heat radiation through the inner wall 360 is less effective. Therefore, it is effective to expose the flange portions 82 outward of the mounting surface A.

Furthermore, outward radiation of heat of the housing 50 can reduce thermal influence on the O ring 90 attached to the housing 50.

A method in which a metal case is connected directly to the housing 50 without use of the resin member, which is susceptible to heat, involves a problem in providing a seal. Specifically, even when the metal case and the housing 50 are laser-welded together full circle, a welding defect is likely to occur, resulting in a failure to provide a sufficient gas tightness. Thus, the following problem may arise: gas to be measured enters the case from a welding defect portion, and a corrosive substance and water contained in the gas cause corrosion or deterioration of the gas sensor element 10, various electrically conductive members, etc.

By contrast, by means of insert molding, the resin member 60 can be joined to the housing 50 in such a manner that gastightness is maintained. Also, since the resin member 60 can assume relatively arbitrary shapes, the length of rearward projection of the gas sensor 200 from the housing 50 can be easily reduced.

Examples of the mounting body 300; i.e., examples of a body to which the gas sensor 200 is to be mounted, include various internal combustion engines; particularly, intake systems of internal combustion engines of vehicles, such as automobiles. The intake system is an intake path extending between an intake to an intake port of an internal combustion engine; for example, an intake pipe or an intake manifold, which branches off from the intake pipe and is connected to the intake port of the internal combustion engine. Intake gas includes fresh air (fresh air which does not contain exhaust) and a mixed gas of fresh air and exhaust refluxed (recirculated) to the intake system.

The gas sensor element 10 of the present embodiment is a so-called full range air/fuel ratio sensor. However, in addition to the full range air/fuel ratio sensor, an oxygen sensor ($\lambda$ sensor) and an $NO_x$ sensor can be used.

As compared with control of an internal combustion engine on the basis of the concentration of a particular gas contained in exhaust detected by a gas sensor provided in an exhaust system, control of the internal combustion engine on the basis of the concentration of a particular gas detected by a gas sensor provided in an intake system exhibits higher accuracy of control of the internal combustion engine. This is because control on the basis of the concentration of a particular gas contained in exhaust is feedback control, whereas control on the basis of the concentration of a particular gas in the intake system is precombustion control.

Next, an example method of manufacturing the gas sensor 200 according to the first embodiment of the present invention will be described with reference to FIGS. 5A to 5E.

First, the front end of the heat sink casing portion 81 of the heat sink member 80 is fitted to the stepped portion 52e (see FIG. 3) of the housing 50 of the element assembly 150 fabricated by a publicly known method. The associated mating surface is subjected to full-circle laser welding, thereby connecting the heat sink member 80 to a rear portion of the housing 50 (FIG. 5A).

Next, the element assembly 150 connected to the heat sink member 80 is placed within an appropriate mold. Then, resin is injected into the mold, thereby insert-molding the resin member body 61 (FIG. 5B). In this case, the connector terminals 70 are provided in such a manner as to be exposed within an internal space of the resin member body 61.

Next, the separator 40 to which the connection terminals 31 and 32 are attached beforehand is fitted to the rear end portion 12 of the gas sensor element 10 disposed within the resin member body 61, thereby connecting the connection terminals 31 and 32 to the corresponding electrode pads 12a and to the corresponding connector terminals 70 (FIG. 5C). In this case, electrical connection is established as appropriate between the connection terminals 31 and 32 and the corresponding connector terminals 70 by spot welding or the like.

Then, the cover 62 is fitted to the opening of the resin member body 61 (FIG. 5D). The cover 62 and the resin member body 61 are joined (e.g., fused) together along a joint J1, thereby providing a seal. The resin member 60 is thus formed. The O ring 90 is externally fitted into the groove D2 (not shown) of the large-diameter portion 52 (not shown), thereby yielding the gas sensor 200 (FIG. 5E).

Next, the configuration of a gas sensor 210 according to a second embodiment of the first aspect of the present invention will be described with reference to FIGS. 6 to 8. The gas sensor 210 is similar to the gas sensor 200 of the first embodiment except that the groove D2 of the housing 50 in the first embodiment is not provided, but a gasket 95 (see FIG. 7) is employed to provide a seal between the gas sensor 210 and the mounting body 300. Configurational features similar to those of the first embodiment are denoted by like reference numerals, and repeated description thereof is omitted.

Figure 6:
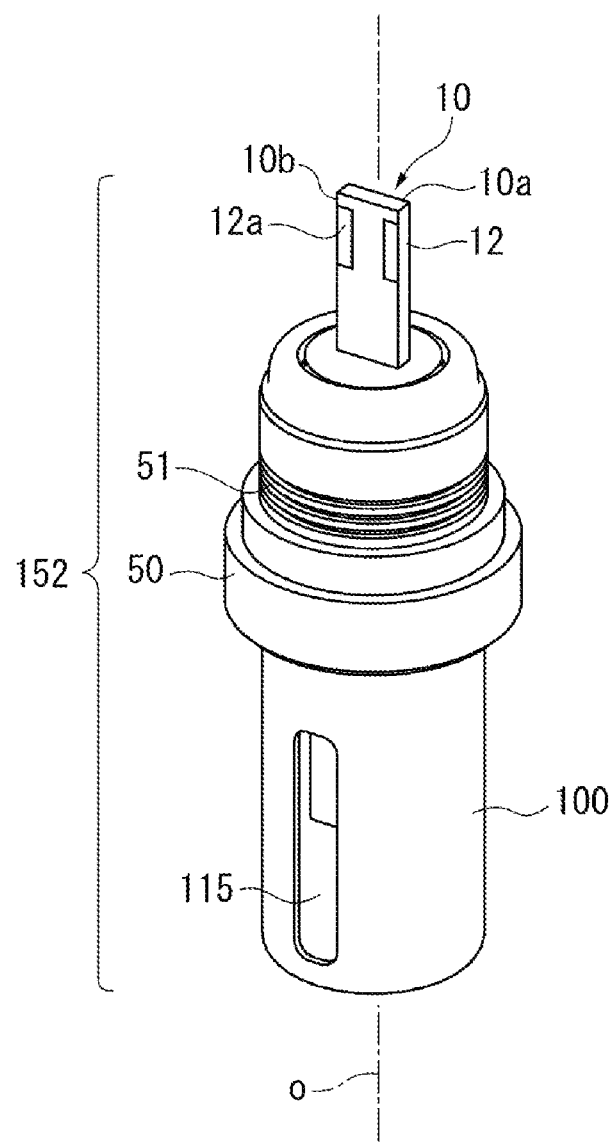
FIG. 6 is a perspective view of an element assembly held within a gas sensor according to a second embodiment of the first aspect of the invention.

FIG. 6 is a perspective view showing an example of the schematic configuration of an element assembly 152 held within the gas sensor 210; FIG. 7 is a perspective view of the gas sensor 210 according to the second embodiment; and FIG. 8 is a sectional view taken along line VIII-VIII of FIG. 7.

Referring to FIG. 6, the element assembly 152 is similar to the element assembly 150 of the first embodiment except for the following: the groove D2 of the housing 50 in the first embodiment is not provided, and the outer stepped subportion of the stepped portion 52e whose diameter is reduced in two steps is higher in the height of step than that of the first embodiment. Thus, the description of the element assembly 152 is omitted.

Figure 7:
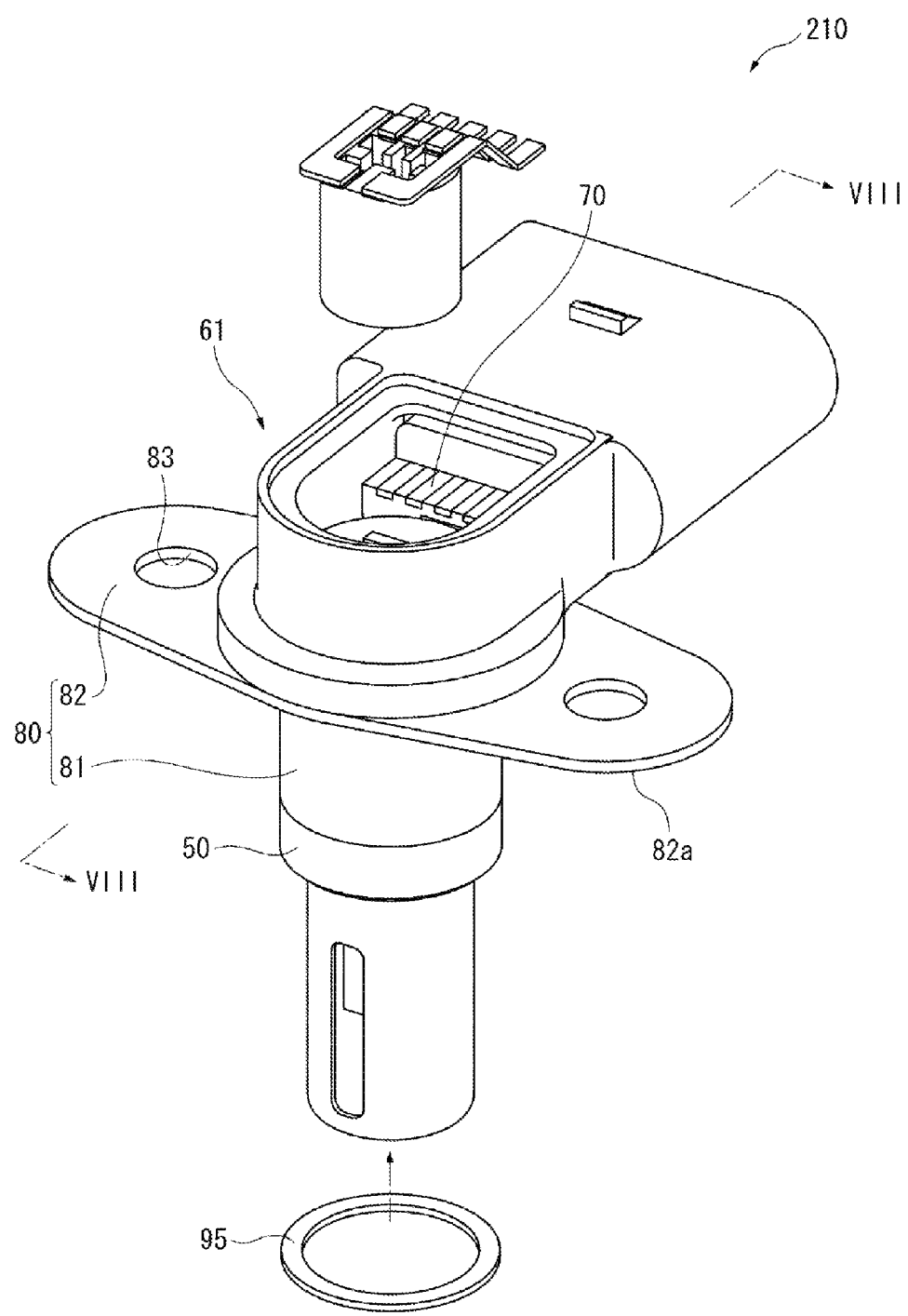
FIG. 7 is a perspective view showing the configuration of the gas sensor according to the second embodiment.

Referring to FIG. 7, the gas sensor 210 is similar to the gas sensor 200 of the first embodiment except that, in place of the O ring 90, a gasket 95 is used to provide a seal between the gas sensor 210 and the mounting body 300. Thus, repeated description of the gas sensor 210 is omitted.

Figure 8:
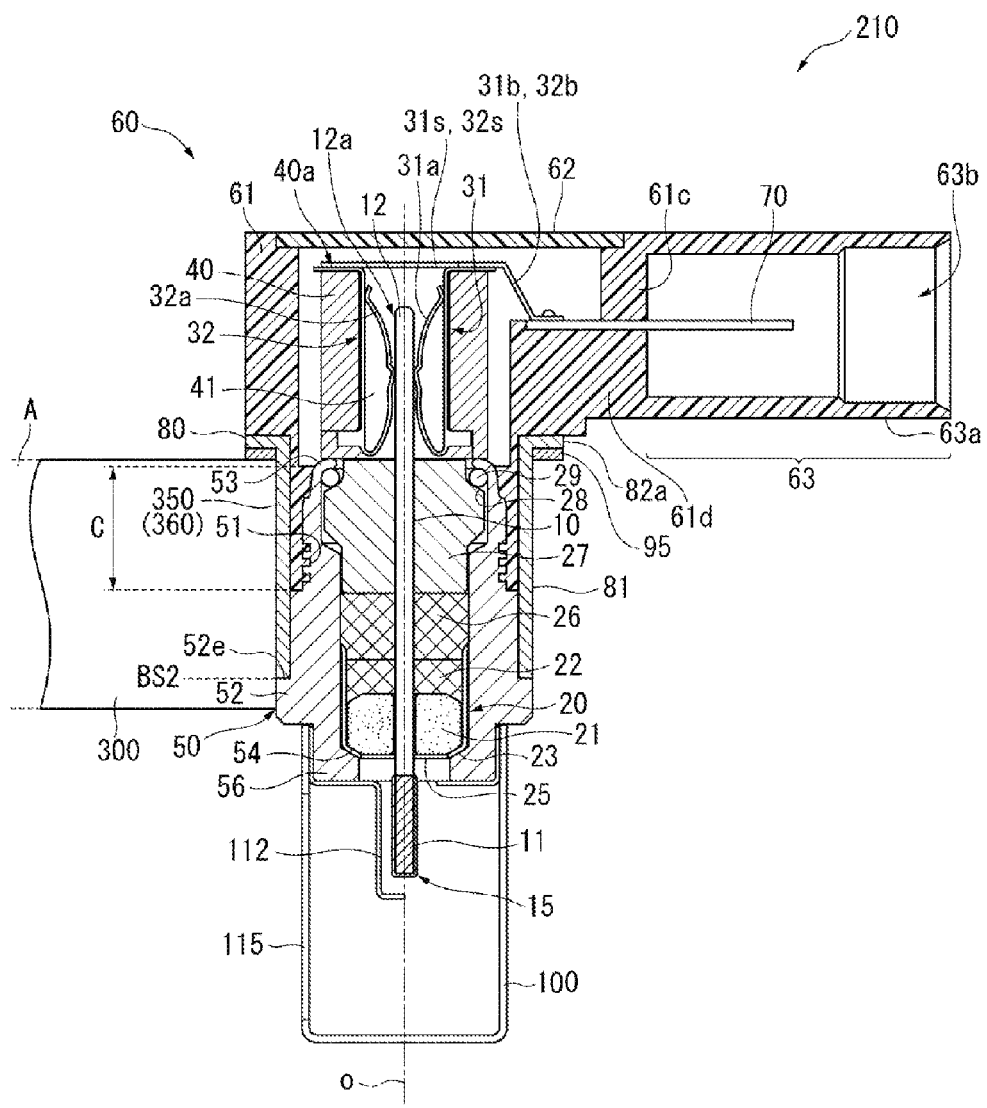
FIG. 8 is a sectional view taken along line VIII-VIII of FIG. 7.

FIG. 8 is a sectional view showing the configuration of the gas sensor 210 and corresponds to FIG. 3 showing the gas sensor 200 of the first embodiment. In FIG. 8, the annular gasket 95 is placed on the frontward-oriented surfaces (back surfaces) 82a of the flange portions 82 and is gastightly in close contact with the outer surface (the mounting surface A) of the mounting body 300.

In the gas sensor 210 also, the outer stepped subportion of the stepped portion 52e of the housing 50 and the front end of the heat sink casing portion 81 mate with each other at the mating surface BS2. A region extending from the inner stepped subportion of the stepped portion 52e to the vicinity of the crimp portion 53 serves as the joint portion C between the resin member body 61 and the housing 50. Furthermore, the entire joint portion C is disposed axially frontward (inward) with respect to the outer surface of the mounting body 300 around the sensor-mounting hole 350 (i.e., the mounting surface A) and corresponds to the "contact portion" of the invention. The heat sink member 80 (the heat sink casing portion 81 thereof) radially surrounds the contact portion (the joint portion C) fully.

In the gas sensor 210 also, at least a portion (in this example, the entirety) of the joint portion C (contact portion) is disposed axially frontward (inward) with respect to the outer surface of the mounting body 300 around the sensor-mounting hole 350 (i.e., the mounting surface A). Thus, the length of outward projection, from the mounting body 300, of the gas sensor 210 including the resin member 60 can be shortened.

The heat sink member 80 (the heat sink casing portion 81 thereof) radially surrounds the joint portion C. Also, while the front end of the heat sink casing portion 81 is in contact with the housing 50 at a position located frontward of the joint portion C, the flange portions 82 integral with the heat sink casing portion 81 are exposed axially outward (rearward) of the outer surface of the mounting body 300 around the sensor-mounting hole 350 (i.e., the mounting surface A). Thus, heat of the housing 50 is radiated axially outward (rearward) of the outer surface of the mounting body 300 around the sensor-mounting hole 350 through the heat sink member 80 (particularly through the flange portions 82). By virtue of this heat transfer mechanism, heat does not stagnate in the joint portion C, thereby reducing thermal influence on the resin member 60 (the resin member body 61).

Next, the configuration of a gas sensor 220 according to an embodiment of a second aspect of the present invention will be described with reference to FIGS. 9 to 11. The second aspect of the present invention is characterized in that a heat sink member 180 surrounds the contact portion from outside and is in contact with the inner wall 360 of the sensor-mounting hole 350.

Figure 9:
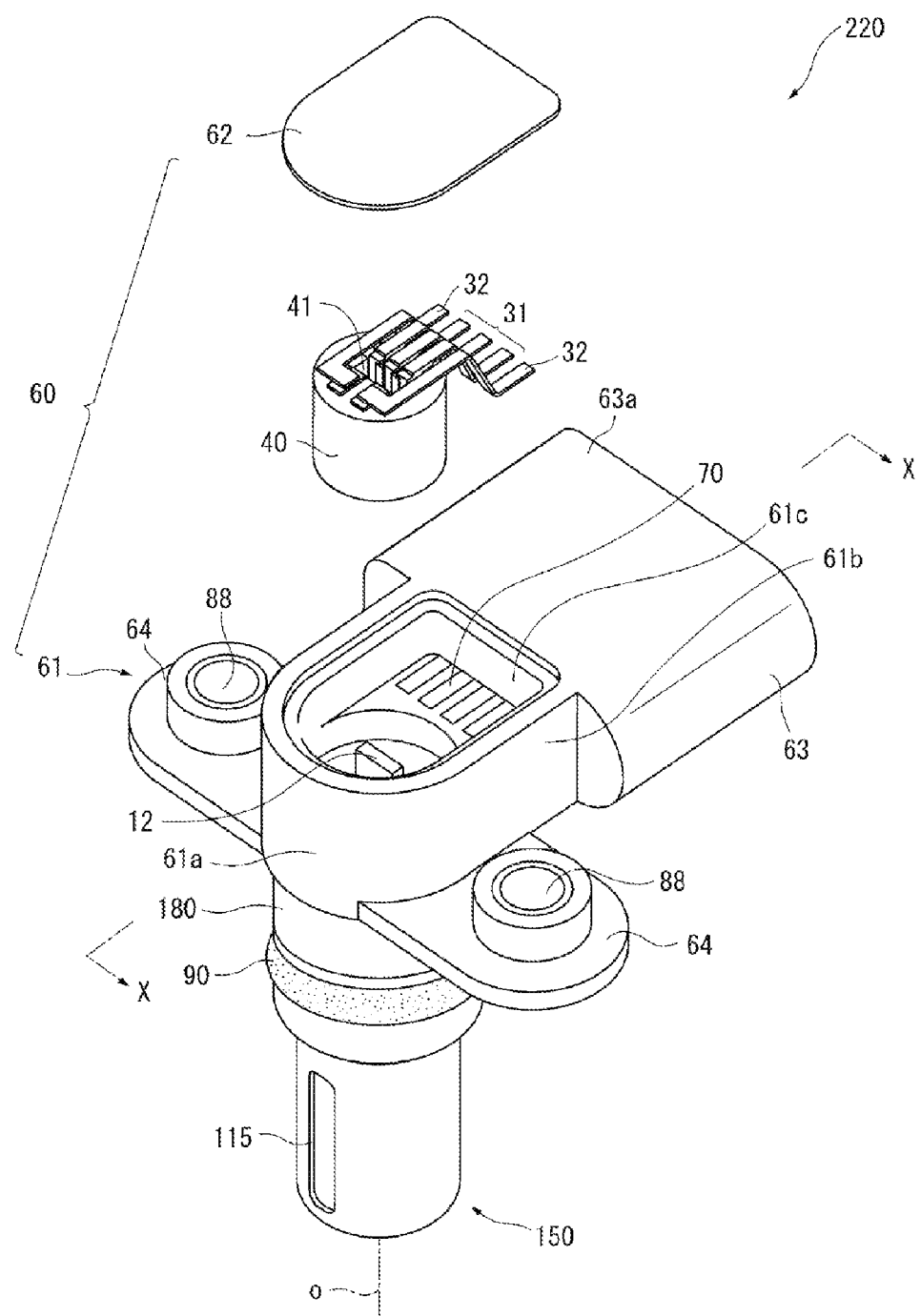
FIG. 9 is a perspective view showing the configuration of a gas sensor according to an embodiment of a second aspect of the invention.

As shown in FIG. 9, the gas sensor 220 is similar to the gas sensor 200 of the first embodiment of the first aspect of the present invention except that, in place of the heat sink member 80 in the first embodiment, the cylindrical heat sink member 180 having no flange portions is employed and that flange portions 64 are resin-molded integral with the resin member body 61. Configurational features similar to those of the first embodiment are denoted by like reference numerals, and repeated description thereof is omitted.

FIG. 9 is a perspective view of the gas sensor 220 according to the embodiment of the second aspect of the present invention; FIG. 10 is a sectional view taken along line X-X of FIG. 9; and FIGS. 11A to 11F are process drawings showing an example method of manufacturing the gas sensor 220.

Referring to FIG. 9, the resin member body 61 is insert-molded to the housing 50 and is thus fixed in place, and the two semicircular flange portions 64 are resin-molded integral with and perpendicularly to the respective wall portions 61b of the resin member body 61. As described below, the flange portions 64 are insert-molded to respective collars 88. Screws are inserted through the respective collars 88 and threadingly engage respective threaded holes formed in the mounting body 300, whereby the gas sensor 220 is mounted to the mounting body 300. In the gas sensor 220, ends of the connector terminals 70 exposed to the internal space of the resin member body 61 are outsert-molded on a ledge portion 61d (see FIG. 10) which protrudes rearward within the internal space of the resin member body 61 and are thus fixed onto the ledge portion 61d.

Figure 10:
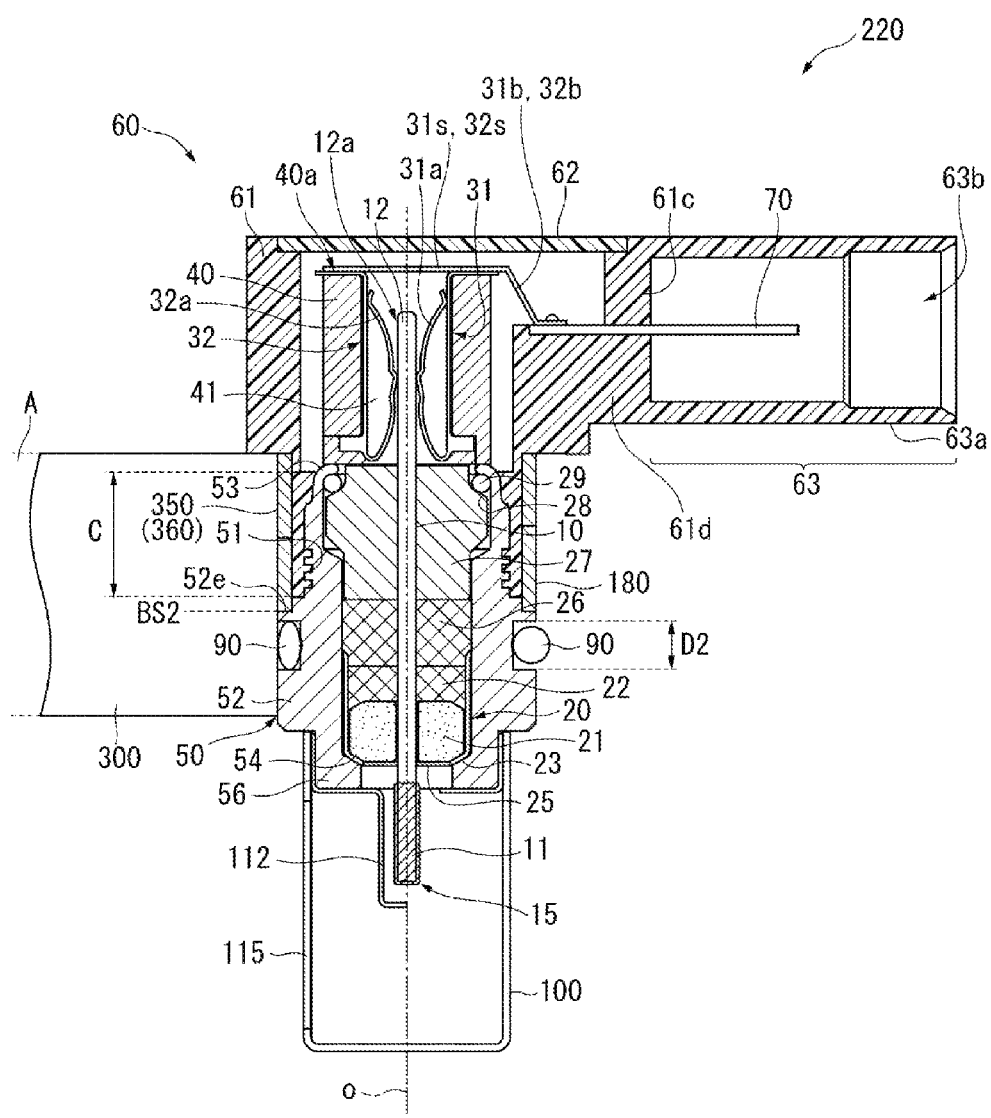
FIG. 10 is a sectional view taken along line X-X of FIG. 9.

FIG. 10 is a sectional view showing the configuration of the gas sensor 220 and corresponds to FIG. 3 showing the gas sensor 200 of the first embodiment. In FIG. 10, the heat sink member 180 has a cylindrical shape and does not have flange portions. The outside diameter of the heat sink member 180 is equal to the outside diameter of the large-diameter portion 52 of the housing 50. The inside diameter of the heat sink member 180 is substantially equal to the outside diameter of the wall surface of an outer stepped subportion of the stepped portion 52e. Thus, when a rear portion of the housing 50 is covered with the heat sink member 180, the front end of the heat sink member 180 is closely fitted to the outer stepped subportion of the stepped portion 52e, and the outer surface of the heat sink member 180 and the outer surface of the large-diameter portion 52 are flush with each other. Furthermore, a clearance corresponding to the radial dimension of the inner stepped subportion of the stepped portion 52e is formed between the inner surface of the heat sink member 180 and a portion of the housing 50 extending from the array of grooves 51 to the crimp portion 53. In this condition, the mating surface BS2 between the stepped portion 52e and the front end of the heat sink member 180 is subjected to full-circle laser welding or the like, whereby the heat sink member 180 radially surrounds a rear portion of the housing 50.

The resin member body 61 is formed through insert molding into the clearance between the housing 50 and the heat sink member 180. The front end of the resin member body 61 is in contact with the inner stepped subportion of the stepped portion 52e of the housing 50. This contact portion is the most frontward portion of contact between the resin member body 61 and the housing 50. The interface between the outer stepped subportion of the stepped portion 52e of the housing 50 and the front end of the heat sink member 180 serves as the mating surface BS2. A region extending from the inner stepped subportion of the stepped portion 52e to the vicinity of the crimp portion 53 serves as the joint portion C between the resin member body 61 and the housing 50. Furthermore, the entire joint portion C is disposed axially frontward (inward) with respect to the outer surface of the mounting body 300 around the sensor-mounting hole 350 (i.e., the mounting surface A). The heat sink member 180 radially surrounds the contact portion (the joint portion C) fully.

On the rear side of the crimp portion 53, the resin member body 61 integrally has a semicylindrical portion 61a provided on the side toward the gas introduction hole 115 of the outer protector 100 and having a diameter greater than that of the large-diameter portion 52 of the housing 50, as well as the wall portions 61b and the connector portion 63.

The semicylindrical portion 61a and the wall portions 61b project radially outward of the heat sink member 180 (the large-diameter portion 52). The frontward-oriented surfaces of the projecting portions of the semicylindrical portion 61a and the wall portions 61b are flush with the frontward-oriented surfaces of the flange portions 64. When the gas sensor 220 is mounted to the mounting body 300, these frontward-oriented surfaces come into contact with the outer surface of the mounting body 300 around the sensor-mounting hole 350 (i.e., the mounting surface A).

Furthermore, the outside diameter of the heat sink member 180 is substantially equal to the diameter of the sensor-mounting hole 350. When the gas sensor 220 is mounted to the mounting body 300, the outer surface of the heat sink member 180 comes into contact with the inner wall 360 of the sensor-mounting hole 350.

In the gas sensor 220 also, at least a portion (in this example, the entirety) of the joint portion C (contact portion) is disposed axially frontward (inward) with respect to the outer surface of the mounting body 300 around the sensor-mounting hole 350 (i.e., the mounting surface A). Thus, the length of outward projection, from the mounting body 300, of the gas sensor 220 including the resin member 60 can be shortened.

Also, while the front end of the heat sink member 180 is in contact with the housing 50 at a position located frontward of the joint portion C between the resin member 60 and the housing 50, the heat sink member 180 is also in contact with the inner wall 360 of the sensor-mounting hole 350. Thus, since most of heat of the housing 50 is radiated to the inner wall 360 of the sensor-mounting hole 350 via the heat sink member 180, the amount of heat transmitted to the resin member 60 is small. Therefore, heat does not stagnate in the joint portion C, which is a portion of the resin member 60 subjected to the highest thermal load, thereby reducing thermal influence on the resin member 60 (the resin member body 61).

Furthermore, outward radiation of heat of the housing 50 can reduce thermal influence on the O ring 90 attached to the housing 50.

Next, an example method of manufacturing the gas sensor 220 will be described with reference to FIGS. 11A to 11F.

Figure 11A:
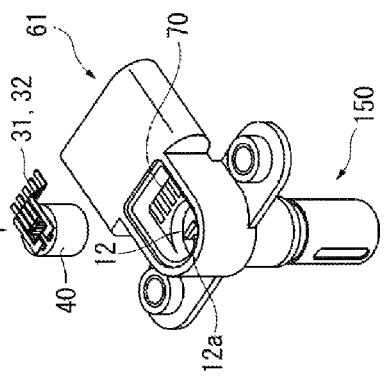
FIGS. 11A to 11F are process drawings showing an example method of manufacturing the gas sensor according to the embodiment of the second aspect of the invention.
Figure 11B:
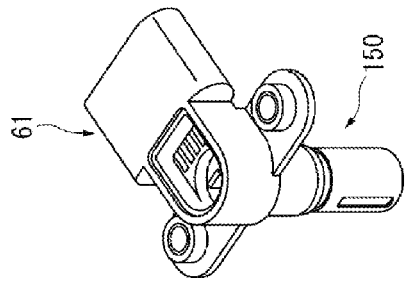
Figure 11C:
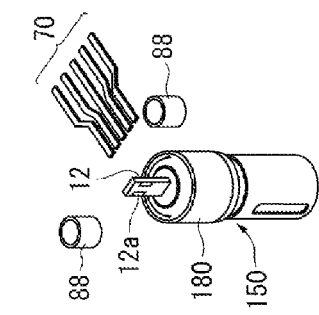
Figure 11D:
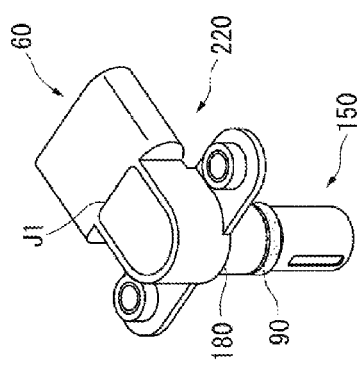

First, the element assembly 150, the collars 88, and the connector terminals 70, which are fabricated by publicly known methods, are placed within an appropriate mold (FIG. 11A). Next, resin is injected into the mold, thereby insert-molding the resin member body 61 (FIG. 11B). Next, the separator 40 to which the connection terminals 31 and 32 are attached beforehand is fitted to the rear end portion 12 of the gas sensor element 10 disposed within the resin member body 61 (FIG. 11C), thereby connecting the connection terminals 31 and 32 to the corresponding electrode pads 12a and to the corresponding connector terminals 70 (FIG. 11D). In this case, electrical connection is established as appropriate between the connection terminals 31 and 32 and the corresponding connector terminals 70 by spot welding or the like.

Figure 11E:
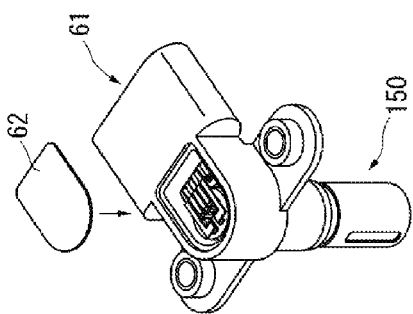
Figure 11F:
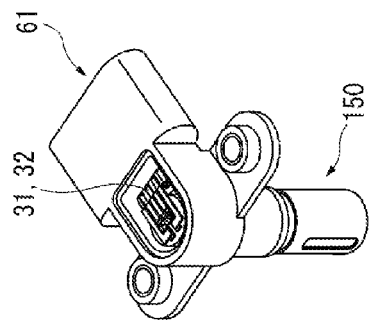

Then, the cover 62 is fitted to the opening of the resin member body 61 (FIG. 11E). The cover 62 and the resin member body 61 are joined (e.g., fused) together along the joint J1, thereby providing a seal. The resin member 60 is thus formed. The O ring 90 is externally fitted into the groove D2 (not shown) of the large-diameter portion 52 (not shown), thereby yielding the gas sensor 220 (FIG. 11F)).

The present invention is not limited to the above embodiments, and may be embodied in an appropriately modified form without departing from the gist of the invention.

Figure 12:
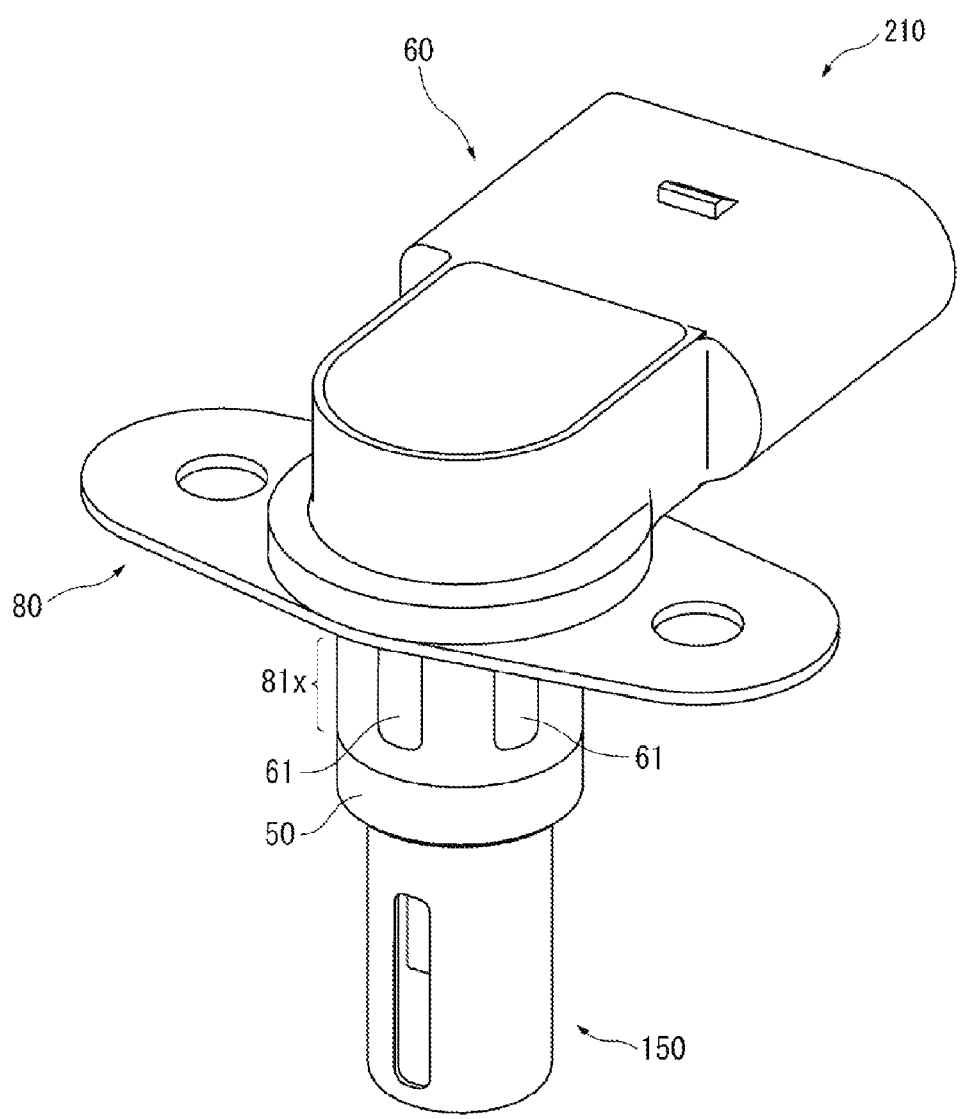
FIG. 12 is a perspective view showing the configuration of a gas sensor in which a heat sink member is provided partially around a contact portion.

For example, according to the example of FIG. 7, the heat sink member 80 (the heat sink casing portion 81 thereof) externally surrounds the contact portion fully. However, the contact portion may be surrounded as shown in FIG. 12. Specifically, while a heat sink casing portion 81x has slits extending in the direction of the axis O, the resin member body 61 is insert-molded, whereby the resin member body 61 is exposed partially through the slits. Also, the slits may extend along the direction of the axis O from the front end to the rear end of the heat sink casing portion 81x. Thermal load is imposed on exposed portions of the resin member body 61; i.e., on exposed subportions of the contact portion. However, when, for example, the working condition of the gas sensor is not severe such that a working temperature condition allows the contact portion to be partially exposed, the modified embodiment of FIG. 12 can be employed.

According to the modified embodiment of FIG. 12, the resin member body 61 and the heat sink casing portion 81x mesh with each other, thereby improving a joining strength therebetween.

Figure 13:
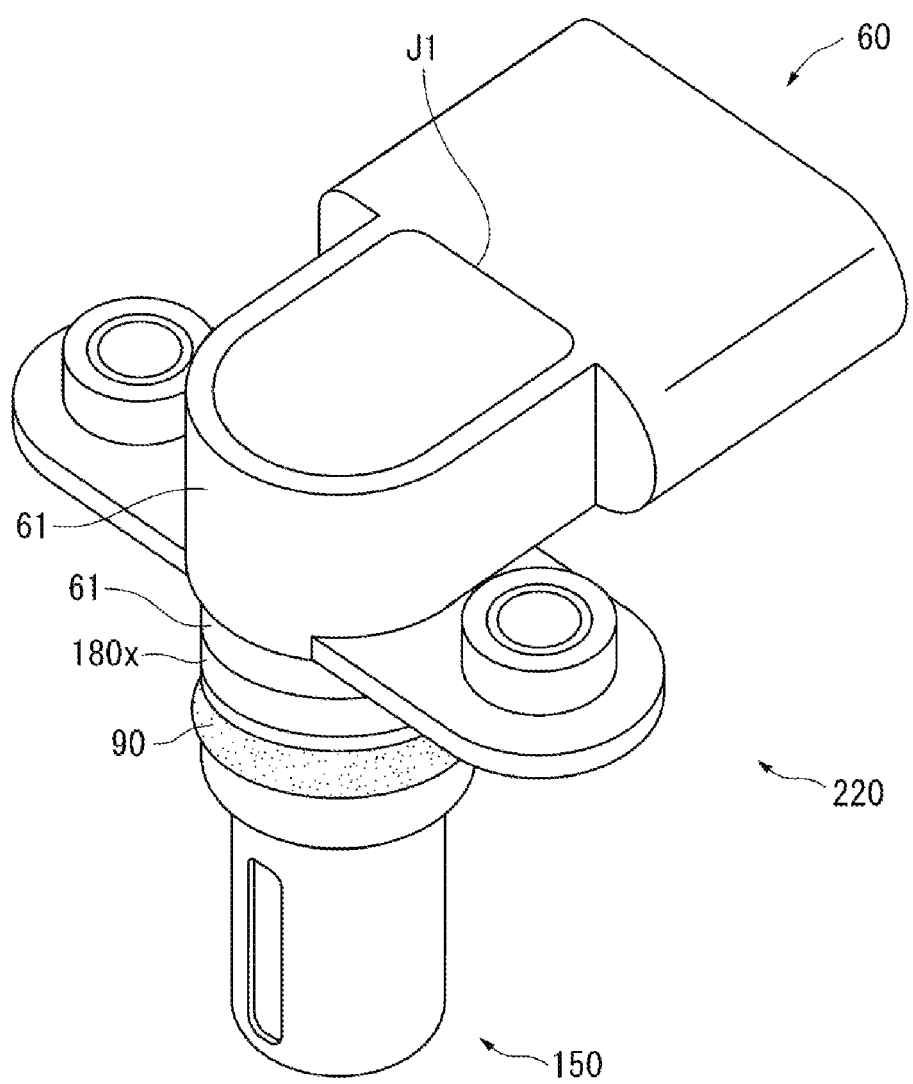
FIG. 13 is a perspective view showing another configuration of the gas sensor in which the heat sink member is provided partially around the contact portion.

According to the example of FIG. 9, the heat sink member 180 externally surrounds the contact portion fully. However, the contact portion may be surrounded as shown in FIG. 13; specifically, while a heat sink member 180x is disposed only at a front subportion of the contact portion C, the resin member body 61 is insert-molded, whereby a portion of the resin member body 61 extends (is exposed) coaxially from the rear end of the heat sink member 180x. Thermal load is imposed on an exposed portion of the resin member body 61; i.e., on an exposed subportion of the contact portion. However, when, for example, the working condition of the gas sensor is not severe such that a working temperature condition allows the contact portion to be partially exposed, the modified embodiment of FIG. 13 can be employed. In this modified embodiment also, slits as shown in FIG. 12 may be formed.

In the modified embodiment of FIG. 13 also, the resin member body 61 and the heat sink member 180x mesh with each other, thereby improving a joining strength therebetween.

In the embodiments described above, the entire joint portion C between the resin member body 61 and the housing 50 is disposed axially frontward (inward) with respect to the outer surface of the mounting body 300 around the sensor-mounting hole 350 and corresponds to the "contact portion" of the invention. However, the joint portion C may partially project axially outward from the outer surface of the mounting body 300 around the sensor-mounting hole 350. This is undesirable because the length of outward projection of the gas sensor from a mounting body increases; i.e., the length of outward projection of the gas sensor from the intake pipe increases. Therefore, preferably, the entire joint portion C is disposed axially frontward (inward) with respect to the outer surface of the mounting body 300 around the sensor-mounting hole 350 (i.e., the mounting surface A).

In the embodiments described above, the resin member 60 is joined to the housing 50 through insert molding. However, the present invention is not limited thereto. The resin member 60 may be joined to the housing 50 through, for example, fitting, such as press fitting or loose fitting, crimping, welding, or fusing.

In addition to the O ring, a sheet packing can be used as the seal member 90. Instead of forming the connector portion 63 integral with the gas sensors 200, 210 and 220, an external connector may be connected to the gas sensors by means of electrically conductive members, such as lead wires and terminals. The conductive members may be partially accommodated within the resin member.

In the embodiments described above, the resin member 60 is molded from a nylon resin. However, the resin member 60 may also be molded from another publicly known resin material.

When the gas sensor of the present invention is mounted to the intake system (e.g., an intake pipe or an intake manifold) of an internal combustion engine, such as a gasoline engine, the gas sensor must be mounted a certain distance away from the engine (a combustion chamber).

In an ordinary engine, fuel is injected from an injector which is mounted to the intake system in the vicinity of a combustion chamber, or within a combustion chamber. Thus, a phenomenon arises in that gas partially flows backward from the combustion chamber to the intake system. Thus, at a position in the intake system near the combustion chamber, a backflow gas coming from the combustion chamber and which contains fuel may exist together with an intake gas (the air and an exhaust gas from an EGR system) which flows in the intake system.

Since the mixture of the intake gas and the backflow gas has an effect on the concentration of a particular gas component (e.g., the concentration of oxygen) contained in the intake gas, the concentration fails to be accurately detected. Thus, control of the combustion condition, etc., is affected. Therefore, when the gas sensor of the present invention is mounted to the intake system, the gas sensor must be located a certain distance away from the engine (a combustion chamber). The distance is adjusted appropriately at the design stage according to, for example, the performance, such as displacement, of the engine and the layout of the intake system. Since the combustion condition can be accurately controlled by means of detecting the concentration of a particular gas component contained in the intake gas immediately before the intake gas is supplied into a combustion chamber, preferably, the position of the gas sensor is closer to the combustion chamber so long as the above-mentioned adverse effect of the backflow gas is not encountered.

It should further be apparent to those skilled in the art that various changes in form and detail of the invention as shown and described above may be made. It is intended that such changes be included within the spirit and scope of the claims appended thereto.

This application is based on Japanese Patent Application No. 2010-164471 filed Jul. 22, 2010, incorporated herein by reference in its entirety.

What is claimed is:

1. A gas sensor comprising:
a gas sensor element extending in a direction of an axis and having a detection portion provided at a front end thereof for detecting a particular gas component in a gas to be measured;
a housing made of metal, the housing radially surrounding the gas sensor element, and adapted for inserting at least partially into a sensor-mounting hole of a mounting body; and
a protector fitted to a front-end engagement portion of the housing for protecting the detection portion,
the gas sensor further comprising:
a resin member which radially surrounds the housing at least partially and having a contact portion in contact with the housing that is at least partially disposed axially frontward with respect to an outer surface of the mounting body around the sensor-mounting hole,
wherein the resin member comprises an insert-molded resin member body fixed to the housing in a gastight configuration, and
a heat sink member that is in contact with the housing at an axial position that is located frontward of an axial position of a front end of the contact portion, and adapted to radiate heat of the housing to the outside of the gas sensor.

2. The gas sensor as claimed in claim 1, wherein the heat sink member is disposed such that a rear end portion thereof is exposed axially outward of the outer surface of the mounting body around the sensor-mounting hole.

3. The gas sensor as claimed in claim 2, wherein the heat sink member is formed such that a rear end portion thereof assumes the form of a flange for mounting to the mounting body.

4. The gas sensor as claimed in claim 1, wherein the heat sink member is disposed such that a portion thereof is in contact with an inner wall of the sensor-mounting hole.

5. The gas sensor as claimed in claim 1, wherein the resin member has a connector portion.

6. The gas sensor as claimed in claim 1, wherein the front end of the contact portion is located between the inner and outer surfaces of the mounting body.

7. The gas sensor as claimed in claim 1, wherein the heat sink member is made of a material having a thermal conductivity higher than that of the resin member.

8. A gas sensor comprising:
a gas sensor element extending in a direction of an axis and having a detection portion provided at a front end thereof for detecting a particular gas component in a gas to be measured;
a housing made of metal, the housing radially surrounding the gas sensor element, and adapted for inserting at least partially into a sensor-mounting hole of a mounting body; and
a protector fitted to a front-end engagement portion of the housing for protecting the detection portion,
the gas sensor further comprising:
a resin member which radially surrounds the housing at least partially and having a contact portion in contact with the housing that is at least partially disposed axially frontward with respect to an outer surface of the mounting body around the sensor-mounting hole,
wherein the resin member comprises a resin member body held in a gastight configuration against the housing, and an array of grooves holds the resin member body in the gastight configuration against the housing, and
a heat sink member that is in contact with the housing at an axial position that is located frontward of an axial position of a front end of the contact portion, and adapted to radiate heat of the housing to the outside of the gas sensor.

* * * * *